United States Patent [19]

Nader

[11] Patent Number: 5,118,431
[45] Date of Patent: Jun. 2, 1992

[54] PHTHALONITRILES AND PHTHALOCYANINES AS LUBRICITY-ENHANCING ADDITIVES

[75] Inventor: Bassam S. Nader, Midland, Mich.

[73] Assignee: The Dow Chemical Company, Midland, Mich.

[21] Appl. No.: 733,578

[22] Filed: Jul. 22, 1991

Related U.S. Application Data

[63] Continuation of Ser. No. 531,966, Jun. 1, 1990, Pat. No. 5,061,388.

[51] Int. Cl.$^5$ ............... C10M 105/70; C07D 487/22; C09B 47/04
[52] U.S. Cl. ............... 252/46.4; 252/46.6; 252/47.5; 252/47; 252/46.7; 252/49.7; 252/49.9; 252/50; 252/51.5 R
[58] Field of Search ............ 252/46.4, 47, 49.7, 252/49.9, 50, 51.5 R, 46.6, 47.5, 46.7; 540/122, 124, 125, 126, 128, 139, 140

[56] References Cited

U.S. PATENT DOCUMENTS

| | | | |
|---|---|---|---|
| 2,122,137 | 6/1938 | Gassner et al. | 540/122 |
| 2,597,018 | 5/1952 | Merker | 252/42.7 |
| 2,795,584 | 6/1957 | Martin et al. | 540/124 |
| 3,023,164 | 2/1962 | Lawton et al. | 252/49.7 |
| 3,432,432 | 3/1969 | Dreher | 252/25 |
| 3,615,558 | 10/1971 | Webster et al. | 540/139 |
| 4,061,654 | 12/1977 | Idelson | 540/125 |
| 4,601,843 | 7/1986 | Carr et al. | 252/78.5 |
| 4,657,554 | 4/1987 | Reinert et al. | 540/140 |
| 4,681,693 | 7/1987 | Gavezotti et al. | 252/49.9 |
| 4,814,256 | 3/1989 | Aldag et al. | 540/128 |

FOREIGN PATENT DOCUMENTS

| | | | |
|---|---|---|---|
| 63-313760 | 12/1988 | Japan. | |
| 0353828 | 6/1961 | Switzerland | 540/126 |
| 1164234 | 9/1969 | United Kingdom | 540/122 |

OTHER PUBLICATIONS

Snow et al., *Syntheses and Characterization of Heteroatom-Bridged Metal-Free Phthalocyanine Network Polymers and Model Compounds*, (1984) vol. 17, Macro., pp. 1614–1624.

Derkacheva et al., *Phenoxy- and (Phenylthio)-Substituted Phthalocyanines*, (1980) vol. 50, Zh. Obshch. Khim., pp. 2313–2318.

Jukes, *The Organic Chemistry of Copper*, (1974) No. 12, Adv. Organomet Chem., pp. 215–322.

*Standard Method of Measurement of Extreme Pressure Prop of Lubricating Fluids (Four-Ball Method)*, ASTM D-2783, vol. 5.02, pp. 424–429.

Still et al., *Rapid Chromatographic Technique for Preparative Separations with Moderate Resolution*, (1978) vol. 43, No. 14, pp. 2923–2925.

Primary Examiner—Margaret Medley
Attorney, Agent, or Firm—Ann K. Galbraith

[57] ABSTRACT

Disclosed herein are phthalonitriles of the following formula:

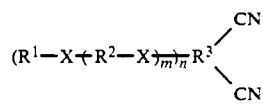

wherein $R^1$, $R^2$, and $R^3$ are independently in each occurrence an aryl or phosphazine group; X is independently in each occurrence O, S, S(O), S(O)(O), P($R^5$), P(O)($R^5$), or N($R^5$); $R^4$ is independently in each occurrence aryl, aryloxy, polyhaloaryl, polyhaloaryloxy, polyhaloalkylaryl, or polyhaloalkylaryloxy; $R^5$ is independently in each occurrence aryl, polyhaloaryl, or polyhaloalkylaryl; n is a number from 1 to 4; and m is a number from 2 to 5. Also disclosed are phthalocyanines prepared from the above-described phthalonitriles. Also disclosed is a lubricant composition which comprises a lubricating fluid and a phthalonitrile or phthalocyanine as described above.

18 Claims, No Drawings

PHTHALONITRILES AND PHTHALOCYANINES AS LUBRICITY-ENHANCING ADDITIVES

CROSS-REFERENCE TO RELATED APPLICATION

This is a continuation of application Ser. No. 07/531,966 filed Jun. 1, 1990, now U.S. Pat. No. 5,061,388.

BACKGROUND OF THE INVENTION

This invention relates to substituted phthalonitriles and substituted phthalocyanines, and to their use as lubricity-enhancing additives in lubricating fluids.

It is generally known that phthalocyanines are useful to enhance the lubricity of lubricating fluids. In addition, phthalonitriles may also be used as additives to enhance the lubricity of lubricating fluids. For example, ortho-phthalonitrile, when suspended or dissolved in a base fluid and subjected to high friction, reacts with metal surfaces at high temperatures to form, in situ, lubricating films of metal phthalocyanines. However, most phthalocyanines do not have melting points, and sublime or vaporize only under extremely reduced pressure and at temperatures exceeding 500° C. These properties essentially preclude the use of phthalocyanines except as insoluble additives in liquid lubricants, or as solid lubricants. Their use as insoluble additives may be undesirable in many applications, because they may not remain suspended in the lubricating fluid during use.

Phthalocyanines and ortho-phthalonitriles which have been substituted with 4-aryloxy substituents are described in Snow, A. W. et al., 17 *Macromolecules* 1614 (1984) and U.S. Pat. Nos. 2,122,137 and 4,061,654. Phenoxy- and thiophenoxy-substituted phthalocyanines soluble in some organic solvents are described in Derkacheva, V. M. et al., 50 *Zh. Obshch. Khim.* 2313 (1980). Fluorine-containing alkoxyphthalonitriles are disclosed in JP Patent App. No. 62-147840. However, these phthalocyanines are not suitable for use as an additive in lubricating fluids which offer high thermal stability.

SUMMARY OF THE INVENTION

In one aspect, this invention is a phthalonitrile of the following formula:

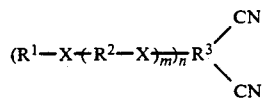

wherein $R^1$ is independently in each occurrence

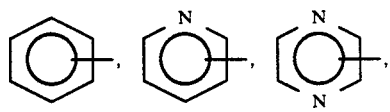

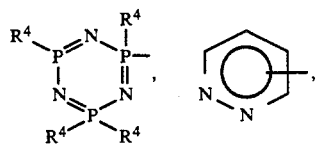

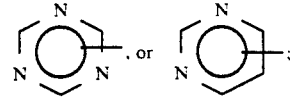

$R^2$ is independently in each occurrence:

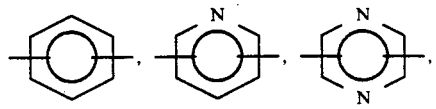

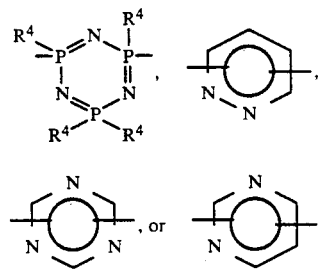

$R^3$ is independently in each occurrence

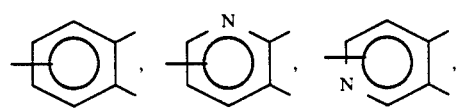

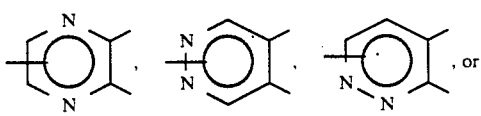

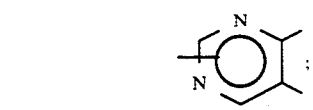

X is independently in each occurrence O, S, S(O), S(O)(O), P($R^5$), P(O)($R^5$), or N($R^5$); $R^4$ is independently in each occurrence aryl, aryloxy, polyhaloaryl, polyhaloaryloxy, polyhaloalkylaryl, or polyhaloalkylaryloxy; $R^5$ is independently in each occurrence aryl, polyhaloaryl, or polyhaloalkylaryl; n is a number from 1 to 4; and m is a number from 2 to 5.

In a second aspect, this invention is a phthalocyanine of the following formula:

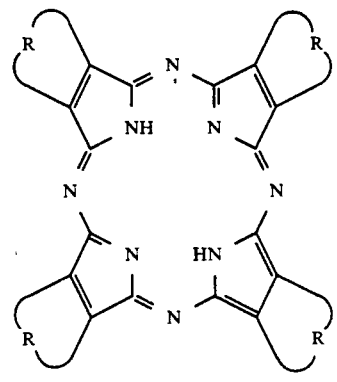

or

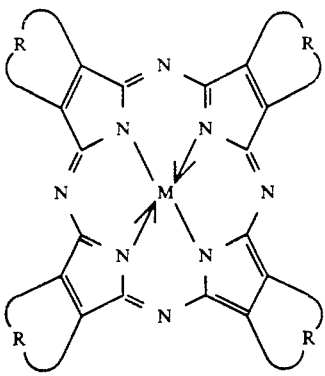

wherein R is independently in each occurrence:

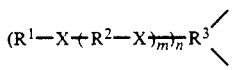

wherein $R^1$, $R^2$, $R^3$, X, m, and n are as defined above.

In a third aspect, this invention is a lubricant composition which comprises a lubricating fluid and a phthalonitrile or phthalocyanine as shown above, wherein the phthalonitrile or phthalocyanine is present in an amount, based on the weight of the lubricating fluid component, of at least about 0.01 percent.

The phthalonitriles and phthalocyanines of the invention are suitable lubricity-enhancing additives for lubricating systems which use fluids stable under high temperatures as a base stock, and are advantageously soluble in such systems. Such lubricant systems are useful in applications over a very wide range of temperatures, such as −50° C. to 500° C. Other utilities for the phthalonitriles and phthalocyanines of the invention include, for example, use as dyes, pigments, soluble electric conductors, photoelectric conductors, electrorheological fluid systems, and as homogeneous organometallic catalysts.

DETAILED DESCRIPTION OF THE INVENTION

The phthalonitriles of the first aspect of the invention are those of the formula:

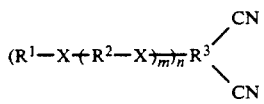

wherein $R^1$, $R^2$, $R^3$, X, m, and n are as defined above. Preferably, $R^1$ is:

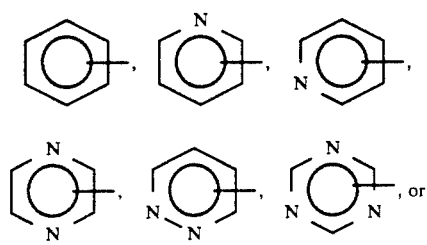

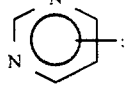

$R^2$ is:

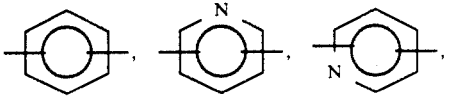

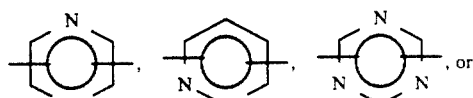

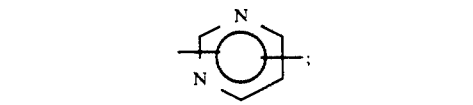

X is O or S, n is 1, and m is 2. More preferably, the phthalonitriles of the invention contain at least one polyphenoxy substituent, wherein X is O, $R^1$ is

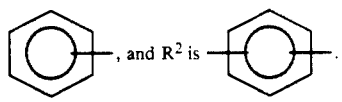

The ring carbons of these compounds which do not have substituents as shown in the formula may optionally be substituted with any other group which would not sterically hinder the reactivity of the phthalonitrile with other phthalonitriles in the formation of a phthalocyanine. Examples of such substituents include alkyl, alkoxy, aryloxy, polyhaloalkyl, polyhaloaryl, polyhaloalkoxy, polyhaloalkylaryl, or polyhaloalkylaryloxy with 1-20 carbon atoms; halogen; aryl; pyridinyl; benzimidazoyl; or benzothiazoyl. Preferably, the ring carbons are unsubstituted or substituted with a $C_{1-10}$ polyhaloalkyl group, since these groups are advantageously more thermally stable. "Phthalonitrile" and "phthalocyanine" as used herein also refers to the analogs of these compounds which contain ring nitrogen atoms, as shown in the above structural formulas for the phthalonitriles.

Examples of phthalonitriles which contain at least one polyphenoxy substituent include 4-(4-phenoxy)-phenoxyphthalonitrile, [3-(3-trifluoromethyl)phenoxy]-phenoxyphthalonitrile, 4-(3-(3-phenoxy)phenoxy)-phenoxyphthalonitrile, 4-(3-phenoxy)phenoxyphthalonitrile, 4-(3-phenoxy-4-trifluoromethyl)phenoxyphthalonitrile, 4-[3-(3-fluoro)phenoxy]phenoxyphthalonitrile, 4-(3-phenoxy-4-fluoro)phenoxyphthalonitrile, 3-(3-phenoxy)phenoxyphthalonitrile, 3-(3-phenoxy-4-trifluoromethyl)phenoxyphthalonitrile, 3-[3-(3-fluoro)phenoxy]phenoxyphthalonitrile, 3-(3-phenoxy-4-fluoro)phenoxyphthalonitrile, 4-(4-phenoxy-3-trifluoromethyl)phenoxyphthalonitrile, 4-[4-(3-fluoro)phenoxy]phenoxyphthalonitrile, 4-(4-phenoxy-3-fluoro)phenoxyphthalonitrile, 3-(4-phenoxy-3-trifluoromethyl)phenoxyphthalonitrile, 3-[4-(3-fluoro)phenoxy]phenoxyphthalonitrile, 3-(4-phenoxy-3- fluoro)phenoxyphthalonitrile, 4-(2-phenoxy)phenoxyphthalonitrile, 4-(2-phenoxy-5-trifluoromethyl)-phenoxyphthalonitrile, 4-[2-(3-fluoro)phenoxy]phenoxyphthalonitrile, 4-(2-phenoxy-5-fluoro)phenoxyphthalonitrile, 3-(2-phenoxy)phenoxyphthalonitrile, 3-(2-phenoxy-5-trifluoromethyl)phenoxyphthalonitrile, 3-[2-(3-fluoro)phenoxy]phenoxyphthalonitrile, 3-(2-phenoxy-5-fluoro)phenoxyphthalonitrile, 3,4-bis[3-phenoxy)phenoxy]phthalonitrile, 4-(2,3-diphenoxy)-phenoxyphthalonitrile, 4-(2,4-diphenoxy)phenoxyphthalonitrile, 4-(2,5-diphenoxy)phenoxyphthalonitrile, 4-(2,6-diphenoxy)phenoxyphthalonitrile, 4-(3,4-diphenoxy)phenoxyphthalonitrile, 4-(3,5-diphenoxy)-phenoxyphthalonitrile, 3-aza-5-[(3-phenoxy)-phenoxy]phthalonitrile, 4-aza-5-[(3-phenoxy)phenoxy]-phthalonitrile, 3,6-diaza-4-[(3-phenoxy)phenoxy]phthalonitrile, 3,5-diaza-6-[(3-phenoxy)phenoxy]phthalonitrile, 3,5-diaza-6-[(3-phenoxy)phenoxy]phthalonitrile, 4-(2-aza-3-phenoxy)phenoxyphthalonitrile, and 4-[3-(2-aza)phenoxy]phenoxyphthalonitrile. Preferably, the phthalonitrile is 4-(4-phenoxy)phenoxyphthalonitrile, [3-(3-trifluoromethyl)phenoxy]phenoxyphthalonitrile, 4-(3-(3-phenoxy)phenoxy)phenoxyphthalonitrile, 4-(3-phenoxy)-phenoxyphthalonitrile, 4-(4-phenoxy)phenoxyphthalonitrile, 4-[3-(3-trifluoromethyl)phenoxy]phenoxyphthalonitrile, 4-[3-(4-trifluoromethyl)phenoxy]phenoxyphthalonitrile, 4-[4-(4-trifluoromethyl)phenoxy]phenoxyphthalonitrile, 4-[3-(3-fluoromethyl)phenoxy]phenoxyphthalonitrile, 4-[3-(4-fluoromethyl)phenoxy]phenoxyphthalonitrile, 4-[4-(3-fluoromethyl)phenoxy]phenoxyphthalonitrile, 4-[4-(4-fluoromethy)phenoxy]phenoxyphthalonitrile, 4-[3-(3-phenoxy)phenoxy]phenoxyphthalonitrile, 4-[3-(4-phenoxy)phenoxy]phenoxyphthalonitrile, 4-[4-(3-phenoxy)phenoxy]phenoxyphthalonitrile, 4-[4-(4-phenoxy)phenoxy]phenoxyphthalonitrile, and is most preferably 4-(3-phenoxy)phenoxyphthalonitrile, 4-(4-phenoxy)phenoxyphthalonitrile, 4-[3-(3-trifluoromethyl)phenoxy]phenoxyphthalonitrile, 4-[3-(4-trifluoromethyl)phenoxy]phenoxyphthalonitrile, 4-[4-(3-trifluoromethyl)phenoxy]phenoxyphthalonitrile, 4-[4-(4-trifluoromethy)phenoxy]phenoxyphthalonitrile, 4-[3-(3-phenoxy)phenoxy]phenoxyphthalonitrile, and 4-[4-(4-phenoxy)phenoxy]phenoxyphthalonitrile.

As used herein, the following terms refer respectively to the generic structures following the term:

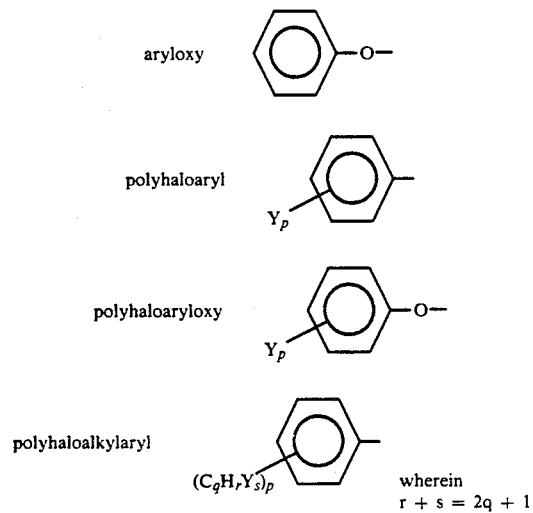

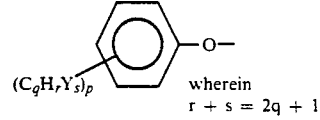

wherein $r + s = 2q + 1$ pyridinyl

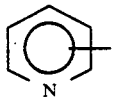

benzimidazoyl

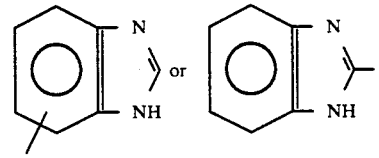

benzothiazoyl

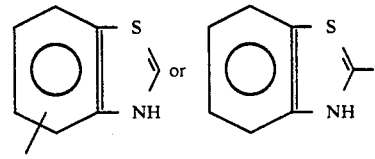

wherein Y is a halo moiety such as, fluoro, chloro, bromo, or iodo; p is a whole number from 1 to 5; and q is a whole number from 1 to 20.

The phthalonitriles of the invention may be prepared from nitro-substituted phthalonitriles, which reaction may be illustrated as follows:

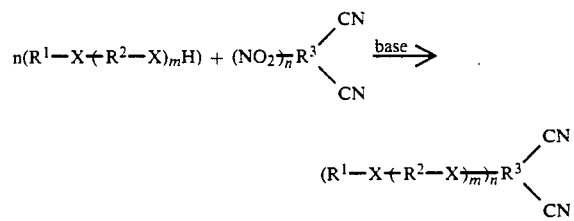

wherein m, n, X, $R^1$, $R^2$, and $R^3$ are as defined above.

The phthalonitriles of the invention which have an ether linkage, i.e., wherein X is —O—, may be prepared by contacting a nitro-substituted phthalonitrile with a phenoxyphenol in the presence of an aqueous or non-aqueous base under reaction conditions sufficient to form the corresponding phthalonitrile with an ether linkage. The phenoxyphenol may contain additional substituents such as, for example, an alkyl, alkoxy, haloalkyl, or haloalkoxy with 1-10 carbon atoms; halogen; aryl; pyridinyl; benzimidazoyl; or benzithiazoyl, but are preferably unsubstituted or substituted with a $C_{1-10}$ perhaloalkyl or $C_{1-10}$ polyhaloalkyl group.

A trifluoromethyl-substituted phenoxyphenol may be prepared, for example, by reacting resorcinol and 3-bromobenzotrifluoride in a solution of sodium methoxide (prepared from a mixture of methanol and sodium). The solvent used in such a reaction is preferably an organic solvent such as, for example, pyridine, benzene, quinoline, diglyme, dimethyl sulfoxide (DMSO), dimethyl formamide (DMF), N,N'-dimethylpyrrolidinone, N,N'-dimethylacetamide, hexamethylphosphoramide (HDMA), sulfolane, or toluene, but is preferably a water-soluble solvent such as pyridine, since such a solvent may be easily removed from the reaction mixture. In addition, this reaction is preferably carried out in the presence of a catalyst such as, for example, a copper salt such as cuprous chloride, or a copper compound as described, for example, in Jukes, A. E. "The Organic Chemistry of Copper" in *Advanced Organometallic Chemistry*, No. 12, pp. 215-321 (1974).

Nitro-substituted phthalonitriles are commercially available, or may be prepared by contacting nitrophthalic acid with ammonia to form a corresponding amide, which may then be dehydrated by the use of a dehydrating agent, such as phosphorous oxychloride, to form a nitrophthalonitrile. Such phthalonitriles may also be prepared, for example, by reacting 4-nitrophthalimide with ammonium hydroxide to form a corresponding amide, which may then be dehydrated by the use of a dehydrating agent, such as phosphorous oxychloride, to form a nitrophthalonitrile.

In the preparation of the phthalonitriles of the first aspect of the invention, the reactions are preferably carried out in the presence of an organic polar aprotic solvent, such as dimethyl sulfoxide (DMSO), dimethyl formamide (DMF), N,N'-dimethylpyrrolidinone, N,N'-dimethylacetamide, hexamethylphosphoramide (HDMA), or sulfolane, and is preferably DMSO. The reaction is also preferably carried out in the presence of a base, such as, for example, potassium hydroxide, sodium hydroxide, or potassium carbonate. Following the reaction, the phthalonitrile may be separated from the reaction mixture through a series of standard filtration and separation techniques to remove the base, solvents, and unreacted starting materials, which are illustrated in the examples which follow.

In a similar manner, the phthalonitriles of the first aspect of the invention which contain thioether (—S—), sulfoxide (—S(O)—), sulfone (—S(O)(O)—), phosphine (—P($R^5$)—), phosphine oxide (—P(O)($R^5$)—), or amine (—N($R^5$)—) linkages may be prepared. The thioethers may be prepared by contacting a thiophenol with a nitrophthalonitrile in the presence of an aqueous or non-aqueous base under reaction conditions sufficient to form the corresponding phthalonitrile containing a thioether linkage. The phthalonitriles which contain sulfoxide and sulfone linkages may be prepared by oxidizing the corresponding phthalonitriles containing thioether linkages. The phthalonitriles containing amine and phosphine linkages may be prepared by contacting a nitrophthalonitrile with an aryl compound containing an amine or phosphine group in the presence of a base under reaction conditions sufficient to form the corresponding phthalonitrile containing an amine or phosphine linkage. The phthalonitriles containing a phosphine oxide linkage may be prepared by oxidizing the corresponding phthalonitrile containing a phosphine linkage.

The phthalocyanine compounds of the invention are those of the following formulas:

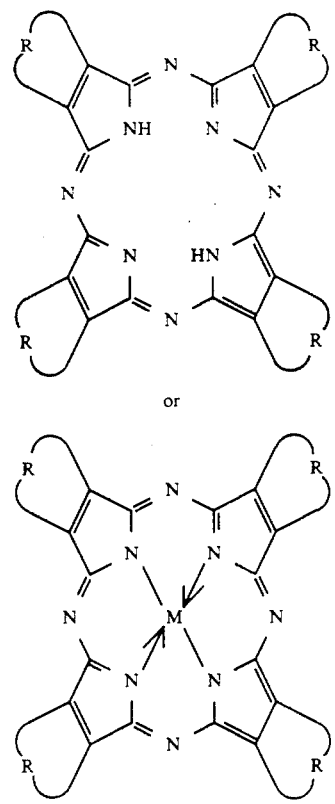

wherein R is separately in each occurrence:

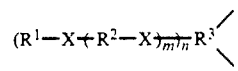

wherein $R^1$, $R^2$, $R^3$, m, and n are as defined above, and M is a metal atom. Preferably, M is lithium, beryllium, sodium, magnesium, aluminum, silicon, potassium, calcium, scandium, titanium, vanadium, chromium, manganese, iron, cobalt, nickel, copper, zinc, gallium, germanium, arsenic, yttrium, zirconium, niobium, molybdenum, technetium, ruthenium, silver, cadmium, indium, tin, antimony, barium, lanthanide, tungsten, gold, mercury, thallium, lead, actinium, thorium, protactinium, uranium, or neptunium and is more preferably zinc, copper, nickel, cobalt, iron, manganese, chromium, vanadium, titanium, or scandium. The term "phthalocyanine" as used herein refers to a metallated or unmetallated phthalocyanine. These phthalocyanines may be prepared by contacting phthalonitriles or phthalimides containing at least one substituent of the formula:

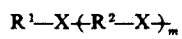

with either a metal salt to form a metallated phthalocyanine, or with a reducing agent to form a metal-free phthalocyanine. Suitable reducing agents include, for example, 1,2,3,6-tetrahydropyridine, lithium alkoxide salts, amyl alcohol, methanol, piperidine, piperazine, and thiazolidine, and is preferably 1,2,3,6-tetrahydropyridine. Phthalimides containing at least one polyphenoxy substituent may be prepared by contacting nitro-substituted phthalic acid esters or amides with aryloxide salt to obtain the corresponding aryloxyphthalic acid esters or amides, followed by conversion to the corresponding phthalimides by ammonolysis.

The most preferred phthalocyanine compounds are those with a 3-(4-phenoxy)phenoxy or a 3-(3-phenoxy)phenoxy substituent, since these advantageously provide the best lubricity, especially when used to enhance the lubricity of a polyarylether lubricant composition. When phthalonitriles are used to prepare the phthalocyanine compounds of the invention, conversion of the phthalonitriles to phthalocyanines will depend on the choice of reducing agent, but is preferably carried out at a temperature in the range of from about 150° C. to about 300° C., and preferably at about 250° C. The conversion preferably takes place under anhydrous conditions, since small amounts of water may give a triazine side-product. The conversion may also be carried out in situ in the lubricating fluid basestock under conditions of high temperature and friction. Under such conditions, the phthalonitriles react with metal-surface asperities at high frictional temperatures to form lubricating films of metallated phthalocyanine. The metallated phthalocyanine may also be formed with hot metal fragments torn from the asperities.

Suitable lubricating fluids which are used with the phthalonitrile and phthalocyanine compounds of the invention include, for example, hydrocarbon lubricants such as mineral oil; alpha-olefin fluids; silicone fluids and greases; polyalkyl ether fluids; perfluoroalkylpolyether fluids and greases; ester lubricants such as pentaerythritol esters; trimethylol alkane esters; polyolesters; polyaryl ether fluids; and phosphazene fluids. Preferably, the lubricating fluid is a phosphazene fluid or polyaryl ether fluid, for their thermal stability. When a phosphazene is used as a lubricating fluid, it is preferably a phosphazene with fluorinated phenoxy and trifluoroalkyl phenoxy groups as described, for example in copending applications Ser. No. 417,363, filed Oct. 5, 1989, which is hereby incorporated by reference in its entirety. Of these phosphazenes, particularly preferred are those wherein the ratio of fluorinated phenoxy groups:trifluoroalkyl phenoxy groups is about 1:2, since such lubricants are useful over extended temperature ranges. Most preferably, the lubricating fluid is a polyaryl ether fluid, since such fluids have high thermal stability.

The phthalonitrile or phthalocyanine compounds are employed in the lubricant composition in a concentration, based on the weight of the lubricating fluid component, of at least about 0.001 percent, more preferably at least about 0.01 percent, and most preferably at least about 0.1 percent; and preferably no greater than about 10 percent, more preferably no greater than about 5 percent, and most preferably no greater than about 1 percent. To prepare a solution of the phthalocyanine compound in the lubricant composition, it is preferable to first dissolve the compound in an organic solvent such as, for example, methylene chloride, and to mix this solution with a solution of the lubricant composition in an organic solvent. The mixture is then preferably filtered to remove solid impurities and any solvents are evaporated from the mixture.

The phthalonitrile and phthalocyanine compounds of the invention provide a lubricant composition with enhanced lubricity, relative to lubricant or heat-transfer systems which do not contain such compounds. Such compounds are especially useful as additives in high temperature lubricant basestocks which may have the thermal stability to withstand high temperature applications, such as in jet aircraft engines, but which have lubricating properties which are less than desired. An example of such a lubricant basestock is a polyarylether fluid. The lubricity of lubricant compositions may be measured by applying a standard test method as described in ASTM D-2783, "Standard Method for Measurement of Extreme Pressure Properties of Lubricating Fluids (Four-ball Method)." In addition, the phthalonitrile and phthalocyanine compounds of the invention are advantageously thermally stable when used in high temperature applications, and are advantageously soluble when used in such systems. Phthalonitriles and phthalocyanines with polyarylether substituents are particularly preferred for use with polyarylether fluid basestocks, due to their enhanced solubility in such fluids.

ILLUSTRATIVE EMBODIMENTS

The following examples are given to illustrate the invention and should not be interpreted as limiting the scope of it in any way. Unless stated otherwise, all parts and percentages are given by weight. All reactions requiring anhydrous conditions are performed in oven-dried glassware which was cooled under nitrogen. Thin layer chromatography (TLC) was performed on glass plates precoated with 0.25 mm of silica gel. Flash chromatography is performed on 230-400 mesh silica gel according to a procedure described in Still et al., 72 *J. Org. Chem.* 3302 (1950). Liquid Chromatography (LC) analyses are performed using a 2.1 mm reverse phase column. Melting points are determined in open capillary tubes, and are uncorrected. For the purposes of recording NMR data, chemical shifts are determined in parts per million (ppm) downfield from Me$_4$Si as an internal standard.

EXAMPLE 1

Preparation of 4-(4-phenoxy)phenoxyphthalonitrile

The reaction is performed in a dry 100-ml 3-necked flask equipped with a magnetic stirring bar, a reflux condenser carrying a nitrogen inlet tube, and two stoppers. The flask is charged with anhydrous dimethyl sulfoxide (DMSO) (50 ml) and purged with nitrogen for 10 minutes. 4-Phenoxyphenol (3.23 g, 17.3 mmoles) and 4-nitro-1,2-dicyanobenzene (3 g, 17.3 mmoles) are added, and purging with nitrogen is continued for an additional 10 minutes. Then K$_2$CO$_3$ (4 g, 36.2 mmoles) is added at ½-hour intervals in one-gram portions. After 14 hours the reaction is complete as shown by thin layer chromatography (TLC). K$_2$CO$_3$ is filtered from the mixture with the aid of CH$_2$Cl$_2$ to remove organic substances from the K$_2$CO$_3$, and the organic layer is washed successively with water (250 ml), saturated NaHCO$_3$ (250 ml) and brine (250 ml), then is dried with MgSO$_4$, and filtered through a column packed with alumina (neutral, Brockman activity 1) eluting with CH$_2$Cl$_2$. This affords 5.16 g (95.6 percent yield, based on the molar amounts of the starting materials) of the desired product as a white crystalline solid, m.p. 118.5° C.-119.5° C. IR (neat film), $^1$H-NMR (CDCl$_3$), and $^{13}$C-NMR (CDCl$_3$) data show the structure to be the title compound, which may be represented by the following formula:

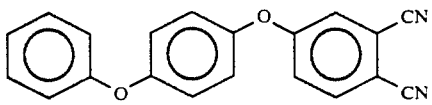

EXAMPLE 2

Preparation of 4-(3-phenoxy)phenoxyphthalonitrile

Following the procedure of Example 1, and substituting 3-phenoxyphenol for 4-phenoxyphenol, 4-(3-phenoxy)phenoxyphthalonitrile is obtained in a 90.6 percent yield. The title compound may be represented by the following formula:

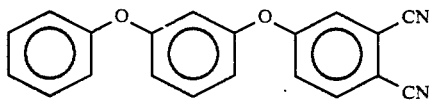

EXAMPLE 3

Preparation of 4-[3-(3-trifluoromethyl)phenoxy]phenoxyphthalonitrile

Preparation of 3-(3-trifluoromethylphenoxy)phenol

All apparatus is rigorously dried and flushed with nitrogen before use. The reaction is performed in a 500-ml 3-necked flask equipped with a mechanical stirrer, a reflux condenser topped with a nitrogen inlet tube and a stopper. The flask is charged with methanol (100 ml) and sodium (10.0 g, 0.43 mole). After all of the sodium has been consumed, the methanol is distilled from the flask, and the last traces are removed by azeotropic distillation with benzene. Pyridine (250 ml) and resorcinol (35.0 g, 0.32 mole) are added to the reaction mixture, followed by 3-bromobenzotrifluoride (50.0 g, 0.22 mole) and cuprous chloride (20 g, 0.20 mole), and the mixture is left to stir at reflux for 24 hours. Capillary gas chromatograph (GC) analysis shows that approximately 87 percent of the mixture is the desired monoalkylation product, the rest being dialkylation product. The mixture is cooled and filtered with the aid of an organic solvent such as ether (200 ml). The ethereal phase is washed successively with water (250 ml), 5 percent HCl (2×500 ml), saturated NaHCO$_3$ (200 ml), and brine (200 ml). It is then dried with MgSO$_4$ and the solvents are removed on the rotary evaporator to leave 38.0 g of a dark oily residue. Purification is accomplished by fractional distillation in vacuo. The second fraction (distilling at 132° C. @ 1.5 mm) consists of pure monoalkylation product (colorless oil, 25.20 g, 44.6 percent yield). The dialkylation product is not isolated. IR (neat film), $^1$H-NMR (CDCl$_3$), and $^{13}$C-NMR (CDCl$_3$) data show the structure to be 3-(3-trifluoromethylphenoxy)-phenol.

Preparation of 4-[3-(3-trifluoromethyl)phenoxy]phenoxyphthalonitrile

Following the procedure of Example 1, the flask containing DMSO is charged with 3-(3-trifluoromethylphenoxy)phenol (4.41 g, 17.3 mmoles) and 4-nitro-1,2-dicyanobenzene (3 g, 17.3 mmoles), and purging with nitrogen is continued for an additional 10 minutes. Then K$_2$CO$_3$ (4.0 g, 36.2 mmoles) is added at ½-hour intervals in one-gram quantities. After 14 hours, the reaction is complete as shown by TLC. The mixture is filtered with the aid of CH$_2$Cl$_2$, and the organic layer is washed successively with water (250 ml), saturated NaHCO$_3$ (250 ml), and brine (250 ml), then is dried (MgSO$_4$) and filtered through a column packed with alumina (neutral, Brockman activity 1) eluting with CH$_2$Cl$_2$. This affords 6.09 g (92.4 percent yield) of the desired product as a white crystalline solid, m.p. 118.5° C.–119.5° C. IR (neat film), $^1$H-NMR (CDCl$_3$), and $^{13}$C-NMR (CDCl$_3$) data show the structure to be [3-(3-trifluoromethyl)phenoxy]phenoxyphthalonitrile, which may be represented by the following formula:

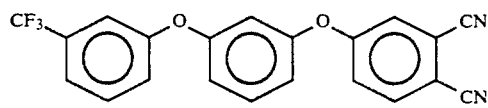

EXAMPLE 4

4-(3-(3-Phenoxy)phenoxy)phenoxyphthalonitrile

Following the procedure of Example 1, the flask containing DMSO is charged with 3-(3-phenoxy)-phenoxyphenol (Kodak, approximately 90 percent purity, remainder 3-phenoxyphenol) (3.22 g, 11.6 mmoles) and 4-nitrophthalonitrile (2 g, 11.6 mmoles), and purging with nitrogen is continued for 10 more minutes. Then K$_2$CO$_3$ (3 g, 21.7 mmoles) is added in one-gram quantities every half hour. After 14 hours the reaction is complete as shown by TLC. The mixture is filtered with the aid of CH$_2$Cl$_2$ (250 ml), and the filtrate is concentrated on the rotary evaporator. Column chromatography on flash grade silica gel using CH$_2$Cl$_2$ as eluent affords 3.47 g (74.3 percent) of the desired product. IR (neat film), $^1$H-NMR (CDCl$_3$), and $^{13}$C-NMR (CDCl$_3$) data show the structure to be 4-(3-(3-phenoxy)phenoxy)phenoxyphthalonitrile, which may be represented by the following formula:

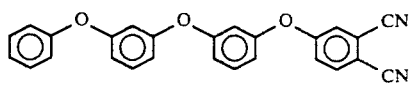

EXAMPLE 5

Tetrakis[4-(4-phenoxy)phenoxy]phthalocyanine 4-(4-Phenoxy)phenoxyphthalonitrile (3 g, 9.6 mmoles) and 12.5 percent molar equivalents of tetrahydropyridine are added to a dry reaction vessel which is then sealed and heated at 250° C. until the phthalocyanine compound solidifies. The title compound (1.94 g, 65 percent) is obtained as a dark purple crystalline solid. The reaction vessel is cooled, and the product is dissolved in CH$_2$Cl$_2$. The solvent is removed on a rotary evaporator and the remaining solid is passed through a short silica gel column using CH$_2$Cl$_2$ as the eluent. The phthalocyanine is a dark purple crystalline solid. FT-IR (evaporated film on NaCl disc) and $^1$H-NMR (CDCl$_3$) data show the product to be tetrakis[4-(4-phenoxy)-phenoxy]phthalocyanine.

EXAMPLE 6

Tetrakis[4-(3-phenoxy)phenoxy]phthalocyanine

Following the procedure of Example 5, and substituting 4-(3-phenoxy)phenoxyphthalonitrile for 4-(4-

Phenoxy)phenoxyphthalonitrile, the title compound is obtained in 72 percent yield.

EXAMPLE 7

Tetrakis[4-{3-(3-trifluoromethyl)phenoxy)phenoxy}]phthalocyanine

Using the procedure of Example 4, [3-(3-trifluoromethyl)phenoxy]phenoxyphthalonitrile (3 g, 7.9 mmoles) yields 1.95 g (65 percent yield) of the title compound which is obtained as a dark purple crystalline solid. Fourier Transform infrared spectroscopy (FT-IR) (evaporated film on NaCl disc) and $^1$H-NMR (CDCl$_3$) data show the product to be tetrakis[4-{3-(3-trifluoromethyl)phenoxy)phenoxy}]phthalocyanine.

EXAMPLE 8

Tetrakis[4-(3-(3-phenoxy)phenoxy)phenoxy]phthalocyanine

Following the procedure of Example 4 and using 2.13 g (5.3 mmoles) of the phthalonitrile of Example 3, 1.25 g (59 percent) of the title compound is obtained as a dark purple crystalline solid. FT-IR (evaporated film on NaCl disc) and $^1$H-NMR (CDCl$_3$) data show the product to be tetrakis[4-(3-(3-phenoxy)phenoxy)phenoxy]phthalocyanine.

EXAMPLE 9

Preparation of tetrakis[4-(3-phenoxy)phenoxy] nickel phthalocyanine

Tetrakis[4-(3-phenoxy)phenoxy]phthalocyanine (0.4 g, 0.32 mmole) and nickel chloride (0.04 g, 0.32 mmole) are stirred in quinoline (15 ml) at 165° C. for 7 hours. The reaction mixture is cooled to room temperature and filtered through a fritted glass funnel (medium frit). The collected blue solid is washed several times with acetone and water, then is dissolved in methylene chloride (50 ml) and filtered through a column of flash grade silica gel (6" by 1" i.d.) using CH$_2$Cl$_2$ as the eluent. The blue filtrate is collected and concentrated under vacuum to around 10 ml. Hexane (150 ml) is added, causing the precipitation of the desired substituted nickel phthalocyanine as a blue solid, which is collected by filtration. (Yield=0.37 g, 88 percent).

EXAMPLE 10

Preparation of tetrakis[4-(3-phenoxy)phenoxy] cobalt phthalocyanine 4-(3-Phenoxyphenoxy)phthalonitrile (5.0 g, 16.0 mmoles) and CoCl$_2$6H2O (0.95 g, 4.0 mmoles) are stirred in ethylene glycol (70 ml) at 190° C. for 3.5 hours. The reaction mixture is cooled to room temperature and filtered through a fritted glass funnel (coarse frit) with the aid of methylene chloride, and the solution is concentrated to about 100 ml under vacuum. Then it is filtered through a column packed with flash grade silica gel (6" by 2" i.d.) using methylene chloride as eluent (3 liters). The solvent is removed under vacuum to leave the desired substituted cobalt phthalocyanine as a blue-purple solid (2.0 g, 38 percent).

EXAMPLE 11

Preparation of tetrakis[4-(3-phenoxy)phenoxy] copper phthalocyanine

4-[3-(phenoxy)phenoxy]phthalonitrile (5.0 g, 16.0 mmoles) and Cu(OH)$_2$ (0.39 g, 4.0 mmoles) are stirred in ethylene glycol (65 ml) for 4 hours at 190° C. The reaction mixture is cooled to room temperature and filtered through a fritted glass funnel (coarse) with the aid of methanol. The collected dark-colored solid is dissolved in a generous amount of methylene chloride and concentrated to about 100 ml under vacuum, then is filtered through a column packed with flash grade silica gel (6" by 2" i.d.) using methylene chloride as eluent (3 liters). The solvent is removed under vacuum to leave the desired substituted copper phthalocyanine as a purple solid (2.0 g, 38 percent).

EXAMPLE 12

Preparation of tetrakis[4-(3-phenoxy)phenoxy] zinc phthalocyanine

4-[3-(phenoxy)phenoxy]phthalonitrile (5.0 g, 16.0 mmoles) and Zn(OH)2 (0.40 g, 4.0 mmoles) are stirred in ethylene glycol (65 ml) for 4 hours at 190° C. The reaction mixture is cooled to room temperature and filtered through a fritted glass funnel (coarse) with the aid of methanol. The collected dark-colored solid is dissolved in a generous amount of methylene chloride and concentrated to about 100 ml under vacuum. The solution is then filtered through a column (6" by 2" i.d.) packed with flash grade silica gel, eluting initially with CH$_2$Cl$_2$ (0.5 liter), then with CH$_2$Cl$_2$-diethyl ether (approx. 10:1 v/v) (3 liters). The solvent is removed under vacuum from the blue filtrate to leave the desired substituted zinc phthalocyanine as a purple solid (1.90 g, 36 percent).

EXAMPLE 13

Preparation of tetrakis[4-(3-phenoxy)phenoxy] iron phthalocyanine

Fe(CO)$_5$ (0.5 ml, 4.0 mmoles) is added dropwise via syringe during a period of 30 minutes to a stirred solution of 4-[3-(phenoxy)phenoxy]phthalonitrile (5.0 g, 16.0 mmoles) in ethylene glycol (70 ml) at 190° C. and the mixture is stirred at 190° C. for 2.5 hours. Then it is cooled to room temperature and filtered through a fritted glass funnel (medium) with the aid of water. The collected dark-colored solid is dissolved in a generous amount of methylene chloride and concentrated to about 100 ml under vacuum. The solution is filtered through a column (8" by 2" i.d.) packed with flash grade silica gel using methylene chloride as the eluent (3 liters). The solvent is removed under vacuum to leave the desired substituted iron phthalocyanine as a purple-black solid (3.8 g, 73 percent).

EXAMPLE 14

Preparation of tetrakis[4-(3-phenoxy)phenoxy] vanadyl phthalocyanine

4-[3-(phenoxy)phenoxy]phthalonitrile (1.3 g, 4.2 mmoles) and VCl$_3$ (0.16 g, 1.0 mmole) are stirred in ethylene glycol (25 ml) for 8 hours at 190° C. The reaction mixture is cooled to room temperature and filtered through a fritted glass funnel (coarse) with the aid of methanol. The collected green-colored solid is dissolved in a generous amount of methylene chloride and concentrated to about 100 ml under vacuum. The solution is filtered through a column (6" by 2" i.d.) packed with flash grade silica gel using methylene chloride as the eluent (1.5 liters). The solvent is removed under vacuum to leave the desired substituted vanadyl phthalocyanine as a dark green solid (0.08 g, 6 percent).

What is claimed is:

1. A phthalocyanine of the following formula:

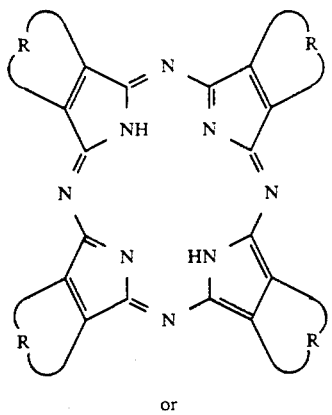

or

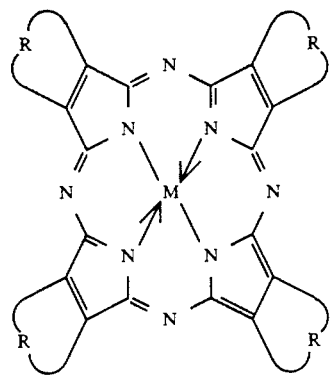

wherein R is separately in each occurrence:

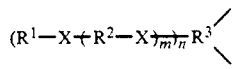

wherein $R^1$ is independently in each occurrence

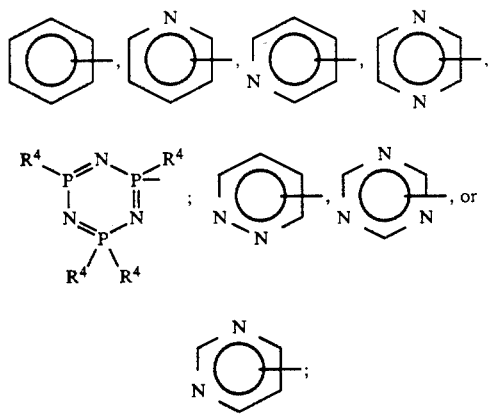

$R^2$ is independently in each occurrence:

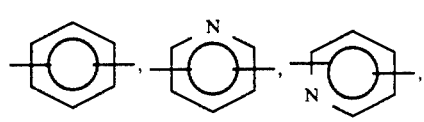

-continued

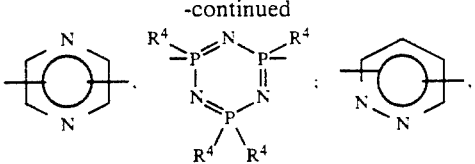

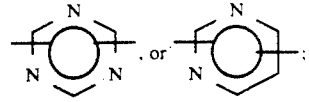

$R^3$ is independently in each occurrence

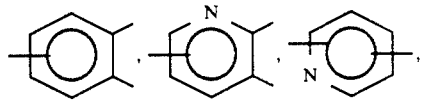

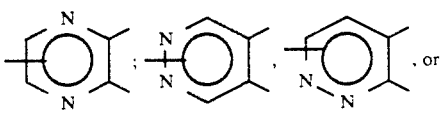

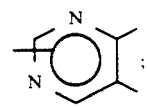

X is independently in each occurrence —O—, —S—, —S(O)—, —S(O)(O)—, —P($R^5$)—, —P(O)($R^5$)—, or —N($R^5$)—; $R^4$ is independently in each occurrence aryl, aryloxy, polyhaloaryl, polyhaloaryloxy, polyhaloalkylaryl, or polyhaloalkylaryloxy; $R^5$ is independently in each occurrence aryl, polyhaloaryl, or polyhaloalkylanyl; n is a number from 1 to 4; m is a number from 2 to 5, and M is a metal atom.

2. The phthalocyanine of claim 1 wherein at least one ring carbon or ring nitrogen of a ring component is substituted with a $C_{1-10}$ perhaloalkyl or polyhaloalkyl group.

3. The phthalocyanine of claim 1 wherein X is —O—.

4. The phthalocyanine of claim 3 wherein $R^1$ is independently in each occurrence

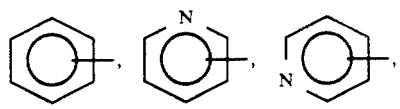

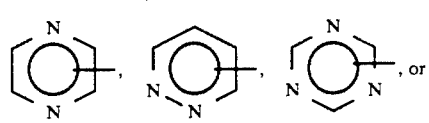

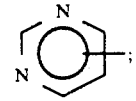

$R^2$ is independently in each occurrence: and

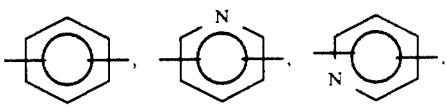

-continued

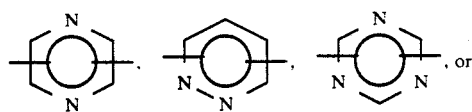

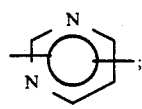

$R^3$ is independently in each occurrence

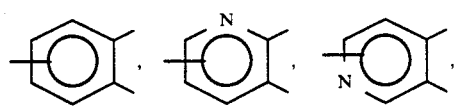

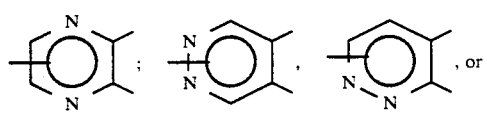

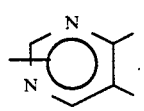

5. The phthalocyanine of claim 3 wherein n is 1 and m is 2.

6. The phthalocyanine of claim 1 wherein $R^3$

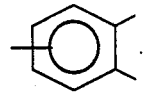

7. The phthalocyanine of claim 1 wherein $R^3$

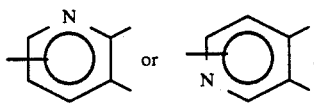

8. The phthalocyanine of claim 1 wherein $R^3$

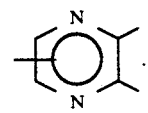

9. The phthalocyanine of claim 1 wherein $R^3$

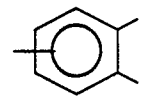

10. The phthalocyanine of claim 1 wherein $R^3$ is

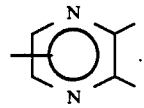

11. A lubricant composition which comprises a lubricating fluid and the phthalocyanine of claim 1, wherein the phthalocyanine is present in an amount, based on the weight of the lubricating fluid component, of at least about 0.01 percent.

12. The lubricant composition of claim 11 wherein the phthalocyanine is present in an amount, based on the weight of the lubricating fluid component, of at least about 0.1 percent.

13. The lubricant composition of claim 11 wherein the phthalocyanine is present in an amount, based on the weight of the lubricating fluid component, of no greater than about 5 percent.

14. The lubricant composition of claim 11 wherein the phthalocyanine is present in an amount, based on the weight of the lubricating fluid component, of no greater than about 1 percent.

15. The lubricant composition of claim 11 wherein $R^3$ of the phthalocyanine is

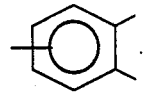

16. The lubricant composition of claim 11 wherein $R^3$ is

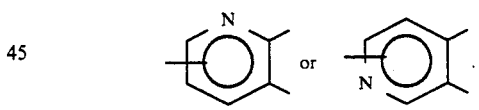

17. The lubricant composition of claim 11 wherein $R^3$ is

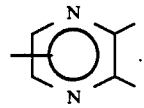

18. The lubricant composition of claim 11 wherein $R^3$ is

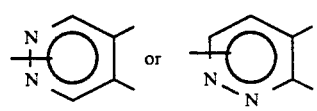

* * * * *